United States Patent [19]
Rose et al.

[11] Patent Number: 5,755,275
[45] Date of Patent: May 26, 1998

[54] TUBED LAMINATION HEAT TRANSFER ARTICLES AND METHOD OF MANUFACTURE

[75] Inventors: Joseph Lorney Rose; Kirk Alan Dobbs, both of Pembroke, Canada

[73] Assignee: Delta Temax Inc., Pembroke, Canada

[21] Appl. No.: 377,827

[22] Filed: Jan. 25, 1995

[51] Int. Cl.$^6$ .................................................... F28F 7/00
[52] U.S. Cl. ........................... 165/46; 165/171; 607/104; 62/259.3
[58] Field of Search .................. 165/46, 171; 62/259.3; 607/104, 108

[56] References Cited

U.S. PATENT DOCUMENTS

| | | |
|---|---|---|
| 3,079,765 | 3/1963 | Le Valentine . |
| 3,174,300 | 3/1965 | Webb . |
| 3,289,748 | 12/1966 | Jennings . |
| 3,400,756 | 9/1968 | Cogswell . |
| 3,425,060 | 2/1969 | Glaser et al. . |
| 3,425,486 | 2/1969 | Burton et al. . |
| 3,430,688 | 3/1969 | Crocker . |
| 3,507,321 | 4/1970 | Palma . |
| 3,670,518 | 6/1972 | Esposito . |
| 3,738,367 | 6/1973 | Hardy . |
| 3,741,849 | 6/1973 | Hardy . |
| 3,743,012 | 7/1973 | Laxo . |
| 3,744,053 | 7/1973 | Parker et al. . |
| 3,758,356 | 9/1973 | Hardy . |
| 4,118,946 | 10/1978 | Tubin . |
| 4,457,295 | 7/1984 | Roehr . |
| 4,677,970 | 7/1987 | Green et al. . |
| 4,718,429 | 1/1988 | Smidt . |
| 4,738,119 | 4/1988 | Zafred . |
| 4,807,447 | 2/1989 | Macdonald et al. . |
| 4,846,176 | 7/1989 | Golden . |
| 4,962,761 | 10/1990 | Golden . |
| 4,998,415 | 3/1991 | Larsen . |
| 5,086,771 | 2/1992 | Molloy . |
| 5,263,336 | 11/1993 | Kuramarohit . |
| 5,269,369 | 12/1993 | Faghri . |
| 5,320,164 | 6/1994 | Szczesuil et al. . |

FOREIGN PATENT DOCUMENTS

| | | |
|---|---|---|
| 2015621 | 10/1991 | Canada . |
| 91 05217 | 10/1991 | France . |
| 2 243 988 | 11/1991 | United Kingdom . |

*Primary Examiner*—Allen J. Flanigan
*Attorney, Agent, or Firm*—Jacobson, Price, Holman & Stern, PLLC

[57] ABSTRACT

A human heat transfer article in the form of pads, blankets, or garments which is a bilayer or trilayer lamination, incorporating flexible fluid-carrying tubes, to contact the skin to modulate the flow of heat to or from the human body, and a method of manufacture therefor. The tubes are stress-relieved to prevent their return to their original configuration. The manufacturing method provides for the mass automated or semi-automated production of flexible, breathable heat transfer pads, blankets, and garments which have fluid-carrying plastic tubing in a self-sustaining, stress-relieved pattern captured between two layers of flexible breathable fabric.

16 Claims, 5 Drawing Sheets

FIG. 3
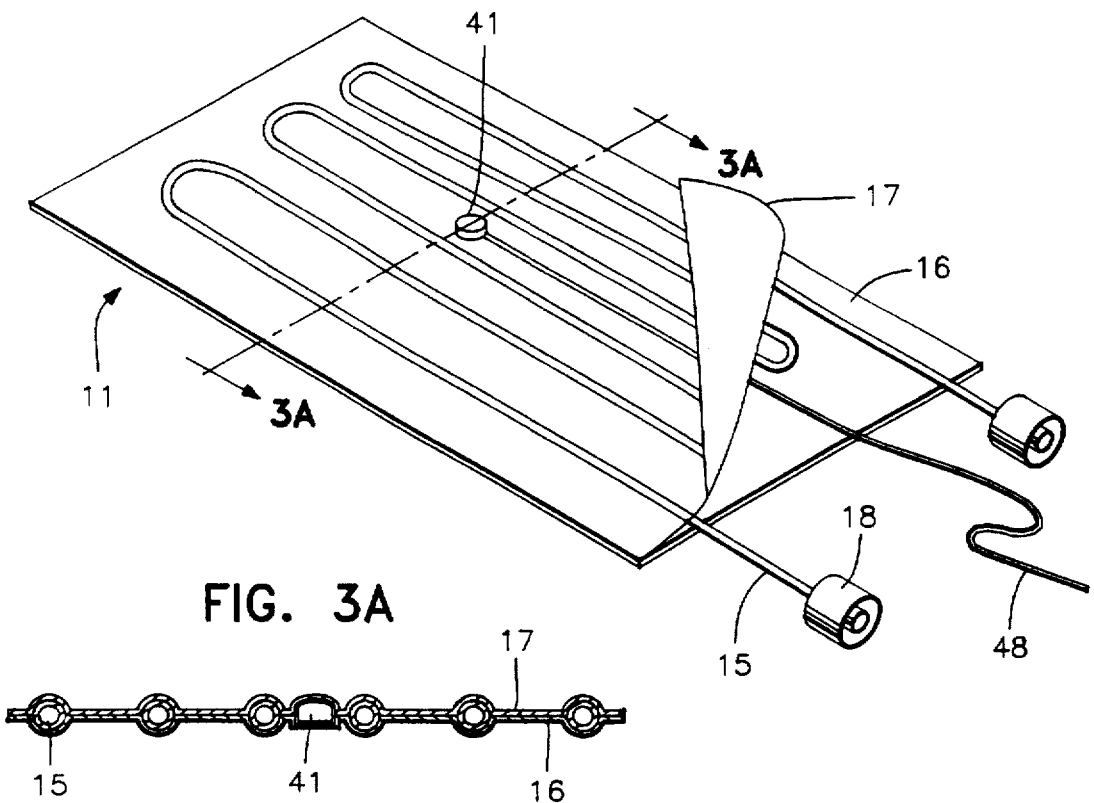
FIG. 3A
FIG. 4
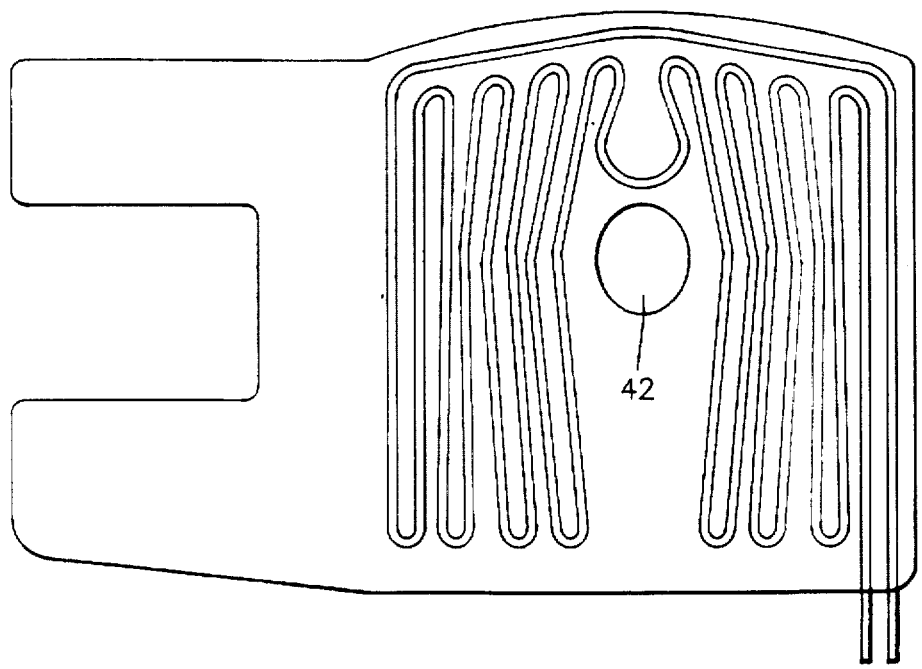

TUBED LAMINATION HEAT TRANSFER ARTICLES AND METHOD OF MANUFACTURE

FIELD OF THE INVENTION

This invention relates to body heating and cooling pads, blankets, and garments, and mass production methods of manufacturing such articles, which provide effective, conductive human heat transfer to a liquid which is circulated through flexible tubing that is captured in a stress-relieved condition between two layers of air and vapor permeable fabric.

BACKGROUND OF THE INVENTION

Much prior art exists that describes various methods of constructing human heat transfer pads, blankets, and garments which contain a labyrinth of conduits designed to carry a circulating liquid which is heated or cooled; the purpose of these pads, blankets, and garments being to add or remove heat conductively to or from the human body. Smaller heat transfer pads are used in medical treatments for localized heating or cooling and various sized blankets are used for the prevention or treatment of hypothermia or hyperthermia. Partial or full-body coverage liquid-circulating heat transfer garments are also applicable to a variety of medical treatments involving the altering or maintenance of body core temperature and are as well used by those people who must perform tasks in extreme thermal environments such as near hot furnaces or outdoors in winter conditions. Extreme thermal "micro-environments" are also created by multi-layer, nonbreathable protective ensembles which trap excess metabolic heat created by the human work, examples of which are rubberized chemical suits worn by firefighters and hazardous materials handlers, and NBC suits (nuclear/biological/chemical) worn by military personnel.

Although many effective liquid-circulating devices have been developed, applied, and currently in use, there are still shortcomings related to cost versus effectiveness which have to-date impeded the widespread use of these products in many applications. It is well known that liquid heating and cooling is more efficient than air due to the much higher thermal conductivity of liquids, such as water, as compared to air, and, it is also well known that a liquid-circulating pad, blanket, or garment should be: a) flexible and stretchable, to conform to the human anatomy so as to be comfortable and not restrict movement, b) breathable, so that the body's natural heat transfer mechanisms are minimally affected, c) thin, so that it does not intefere with the use of other devices or garments, d) effective at conductively adding or removing heat, and e) cost effective. To-date, two basic methods of constructing liquid-circulating human heat transfer pads, blankets, and garments have shared a modicum of success in the marketplace.

The first method involves the use of two layers of heat sealable, plasticized materials which are welded together in such a way as to form a labyrinth of channels through which the liquid may flow. These are generally referred to as bladder devices and, although they do provide for effective conductive heating or cooling, these bladder pads suffer from the fact that they are not stretchable, conforming, or breathable; drawbacks that are well known even to those companies that manufacture such devices. Another disadvantage of bladder pads is that they can easily suffer from pressure induced occlusions which block the flow of liquid thereby causing the thermal effect to be negated in the occluded area. The advantage of bladder type devices is that they do lend themselves to mass production and therefore meet the requirement of cost effectiveness. Bladder type heat transfer pads are exemplified by TEMP-PAD Localized Cold Therapy Pads manufactured by Seabrook Medical Systems, Inc. and bladder type blankets are exemplified by PLASTI-PAD and MAXI-THERM Hypo/Hyperthermia Blankets manufactured by Cincinnati Sub-Zero Products, Inc.. Bladder type garments are exemplified by COOLVEST manufactured by ILC Dover, Inc.

The second method involves the fixation of small diameter, flexible, liquid-carrying, plastic tubing (typically polyvinyl chloride) to a breathable, stretchable fabric by means of stitching and are generally referred to as tubed devices. Tubed pads, blankets, and garments can be single or multiple fabric layer construction and have the advantage of excellent anatomical conformity while still allowing the body to auto-regulate thermally because the fabric is air and vapor permeable. They also are lighter than bladder devices because of the reduced volume of liquid which needs to be in the tubing network and therefore do not overencumber the wearer. In fact, whole-body and partial-body garments made in this fashion are in use in industrial, motorsports, and defense applications and have been shown to have good heat transfer ability and minimal effect on wearer flexibilty and mobility. Tubed human heat transfer garments made in this general way are described in the prior art such as, but not limited to, U.S. Pat. Nos. 3,289,748, 3,425,486, 3,430,688, 3,744,053 and 3,738,367, and more specifically in published Canadian Patent Application No. 2015621, published Oct. 27, 1991, and its counterpart patents U.K. Patent GB 2,243, 988 and France Patent 91 05217 and are exemplified by heat transfer garments manufactured by Delta Temax, Inc. (formerly Exotemp Ltd. of Canada). There are shortcomings related to this technology as well. Needle holes throughout the device are unavoidable and in heat transfer garments which are made for special chemical resistant applications these needle holes can provide an unwanted path for harmful chemicals. In addition, because the tubing is stressed into a serpentine configuration the substrate fabric needs to be substantial enough to prevent the device from becoming shape-distorted, when in fact, in most applications it is desireable to keep the device as thin and supple as possible. Another shortcoming of stitching tubed devices is that it is quite labor intensive, not lending itself to mass automated or semi-automated production, and therefore, the resulting manufacturing costs are high.

Another basic method of constructing liquid-circulating heat transfer garments is disclosed in U.S. Pat. No. 5,320, 164 which contemplates a process for capturing liquid-carrying tubing between two layers of flexible, breathable fabric, at least one layer of which is a heat fusible fabric having fusible adhesive dots thereon to produce a heat transfer garment which is allegedly flexible, conforming, breathable, needle hole free, and cost-effective to produce. However, there are a number of disadvantages with the use of heat fusible fabric in heat transfer garments having liquid-carrying tubing. Fusible fabrics use thermoplastic hot-melt adhesives which fall into three major groups - polyethylenes, polyamides, and ethylene-vinyl acetate copolymers which are all applied molten and bond simply by solidification. Fusible fabrics require that heat and pressure be applied coincidentally to melt the thermoplastic adhesive and allow the adhesive to bond to the non-fusible mating fabric. This task is straightforward for laminating flat (essentially two dimensional) materials. However, when tubing, a component with considerable depth, is introduced into the center of the lamination, this step of applying heat and pressure is radically more complicated. To make the two pieces of fabric meet intimately during the heating cycle would require a special head or fixture which would have to be, for example, grooved in a pattern the same as the tubing, thereby allowing pressure and heat to be applied to the fabrics only, while holding the tubing in the proper position. Given the fact that the tubing network is a complex shape with tubing running in both latitudinal and longitudinal directions, fixtures and production equipment would become needlessly complicated and expensive. Normal fusing equipment such as hot presses or heated rollers will simply not allow uniform, intimate contact of the lamination fabrics due to the thickness of the tubing (typically 0.064 inch even if completely flat ie., two wall thicknesses) and as well, the thermoplastic hot-melt adhesives are heated to temperature ranges at which the thermoplastic tubing can be permanently deformed or damaged, for instance 300° F. as noted in U.S. Pat. No. 5,320,164. Also, this high temperature fusing method severely limits the types of substrate and liner fabrics which can be used to only those thick enough or heat resistant enough to withstand this harsh treatment. In addition, using the method of U.S. Pat. No. 5,320,164 requires the adhesive to be agressive enough and applied in quantities sufficient to permanently restrain the tubing against its natural tendency to return to its originally extruded substantially straight line shape. If these stress-induced forces could be eliminated the demands on the adhesive would be lessened, thereby making it easier to produce a device with maximum suppleness and breathability.

In summary, it is important to provide heat transfer pads, blankets, and garments which do not restrict the body's natural evaporative process and allow convective heat transfer while still providing sufficient surface area contact with liquid-carrying conduits to provide for effective, conductive heat transfer. Tubing affixed to a breathable substrate or sandwiched between two breathable layers using an adhesive as the mechanical means for holding the tubing network onto a supporting fabric holds the most promise to achieve the optimum in cost versus effectiveness. However, any method contemplated needs to ensure that the amount, type and application of the adhesive is optimum so as not to adversely affect breathability, flexibility, and manufacturing costs.

SUMMARY OF THE INVENTION

The present invention relates to a new and improved laminated tubed heat transfer pad, blanket, and garment and an innovative method for the cost-effective production of such pads, blankets, and garments that meet previously described requirements and overcome the disadvantage of the prior art. In the preferred embodiment of the invention, a number of tubing fixtures are used to temporarily hold the plasticized PVC tubing in the desired configuration until it can be, a) thermally treated and, b) transferred to the substrate fabric. These tubing fixtures use an array of pins mounted in a base plate to form "gates" to hold the tubing in the desired configuration. The tubing is elevated in temperature as the loaded tubing fixtures, travelling on a conveyor, pass through a radiant heating chamber. The applied heat raises the tubing temperature to approximately 300° F. for a brief period following which the tubing is immediately cooled in a forced-air cooling chamber. This heating and cooling treatment causes the tubing to take on a new self-sustaining shape, that shape being the desired serpentine configuration; ie., the tubing is stress-relieved.

This stress-relieving treatment is very important because without it the tubing will exhibit a strong tendency to migrate (by trying to straighten out) and may even later kink (at tight radius bends) when it is transferred to the substrate fabric and removed from the fixture.

Once the tubing fixtures (which are like cassettes) are out of the thermal treatment process they are loaded in sets (typically two to six) onto a fixture holder on the main production line, this fixture holder having the ability to be actuated in such a way as to move the tubing fixtures (tubing facing substrate fabric) in contact with the substrate fabric. The substrate fabric has been pre-coated with a "high tack" adhesive at the start of the main production line. The adhesive is aggressive enough to both hold the tubing in place during the lamination process and produce a positive bond between the two fabric layers. The adhesive in the preferred embodiment is a thermosetting polyurethane, more specifically a moisture-curing, aliphatic with a fast setting speed and is applied by a multiple-head, air dispersed (or controlled fiberization) method. This method warms the adhesive and using air produces a thin monofilament strand of adhesive which is laid down in a consistent helix pattern. Other embodiments may use thermoplastic pressure sensitive adhesives, and solvent or water-based rubber-type adhesives and other adhesive dispensing systems such as single head air atomized spray, electrostatic spray, drip, brush or roller feed. Adhesives can also take the form of so called transfer tapes which are essentially thin porous films of adhesive supported on removable paper or adhesive powders which are uniformly distributed onto the substrate and later heated to react them. The preferred polyurethane, in a cured state, is very flexible, very strong per unit mass, non-toxic and non-hazardous and allows the use of virtually any substrate and liner fabric combination.

Once the tubing has come in firm contact with the adhesive-coated substrate fabric, pressure on the fixture holder is removed and the tubing release plates are disengaged forcing the tubing network to part from the base plate of the fixture and remain on the substrate fabric. At this point, in one embodiment of the invention, a temperature sensor is placed on the substrate fabric between and away from the fluid-carrying tubing. The purpose of the sensor is to measure the temperature of the user's skin and use that measurement for the manual or automatic control of liquid delivery temperature or flow rate to achieve the desired result. The liner fabric is then compressed onto the substrate fabric containing the tubing using a series of compression rollers and thus completing the lamination process. Following lamination, the laminated strip is cut into individual product pieces by a power knife.

The heat transfer pad, blanket, or garment thus includes a stress-relieved flexible tubing disposed in a serpentine configuration. The utilization of a stress-relieved tubing has a significant advantage over the prior art tubing arrangements, which require aggressive bonding or sewing to prevent the tubing from "returning" to its original normally straight, position.

BRIEF DESCRIPTION OF THE DRAWINGS

FIG. 3 is a perspective drawing of the laminated thermal therapy pad.

FIG. 3A is a cross-section taken along line A—A of FIG. 3.

FIG. 4 is a plan view of a laminated thermal therapy knee pad.

DETAILED DESCRIPTION OF A PREFERRED EMBODIMENT

Figure 1:
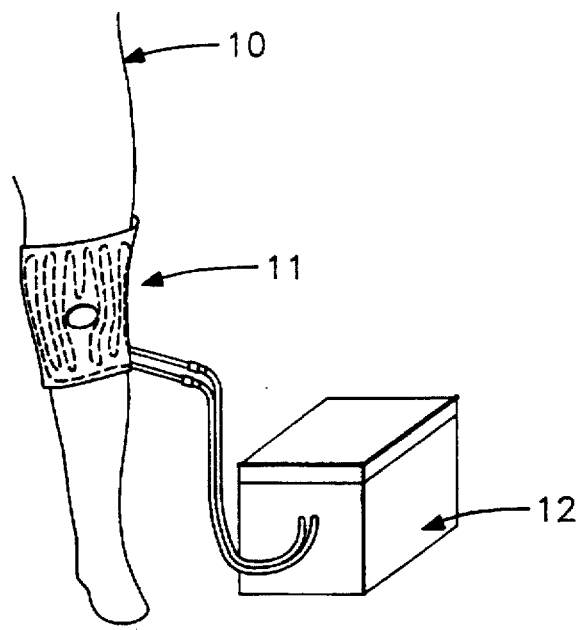
FIG. 1 is a representation of a typical localized thermal therapy pad.

FIG. 1 shows a patient 10, wearing a thermal therapy pad 11, on the knee. The pad is connected to a heating/cooling unit 12, which supplies the temperature-controlled liquid through the tubing within the pad 11. Such heating/cooling units 12 are well-known in the art. In this application the purposes of the product are to reduce pain and swelling and promote healing. The thermal therapy pad of the present invention has an anatomically specific tubing pattern to direct the thermal treatment to where it is indicated. Because the pad is so thin, it can be worn underneath other clothing, or immobilizing devices such as braces or casts. Due to the breathability of the pad, it provides little thermal burden when liquid is not flowing and because it is flexible it can be worn for lengthy periods without discomfort.

Figure 2:
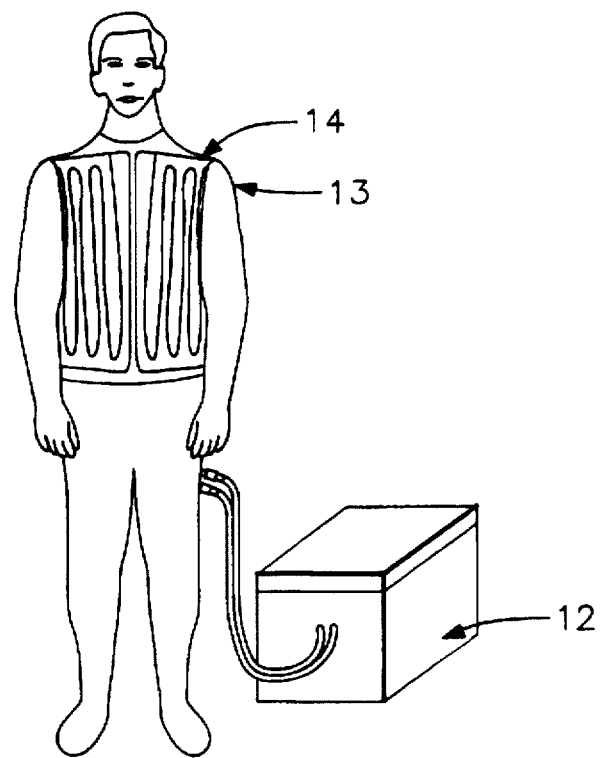
FIG. 2 is a representation of a heating/cooling vest used to alter or maintain body core temperature.

FIG. 2 shows a person 13, wearing a heating or cooling garment in the form of a tubed vest 14. The heating/cooling unit 12, can be umbilical in nature as shown or person-portable in nature (not shown) for added mobility, both arrangements known in the art. A vest made in accordance with the subject invention costs a fraction of the same product made using the stitching method, and is cost comparable to a bladder device yet maintaining all of the inherent advantages of a breathable, flexible tubed device.

FIGS. 3 and 3A illustrate the laminated heat transfer pad 11, with stress-relieved flexible tubing 15, disposed in a self-sustaining serpentine configuration and sandwiched between substrate 16, and liner 17, fabrics. Opposite ends of the tubing 15 extend outwardly from the substrate 16 and liner 17 and are attached, in a known manner, to connectors 18 which are, in turn, connected to the input and output tubings of the heating/cooling unit 12. A temperature sensor 41, which may be a component of the pad in certain embodiments of the invention for more critical applications, is placed in between the fluid-carrying tubes so as not to reflect the temperature of the pad or the tubing but instead to indicate the temperature of the user's skin. The electrically conductive leads 48, extend out of the lamination and may be connected to an electronic temperature measuring unit (not shown) as is well-known.

In another embodiment, not shown, the construction may be simplified by not utilizing a liner fabric. The stress-relieved tubing is only fixated to the substrate fabric using an adhesive thereby allowing direct tubing-to-skin contact and therefore maximum heat transfer. This alternative bicomponent construction may be preferable for cost reduction purposes, especially in a limited use or disposable product application.

FIG. 4 shows a laminated thermal therapy pad used for knee treatment and exemplifies the ability of the subject invention to direct the thermal therapy to anatomically-specific sites. This particular pattern allows the thermal treatment to take place in the fatty tissues surrounding the affected area but avoiding bony prominences 42, where thermal therapy is contraindicated. By stress-relieving the tubing, in a manner as discussed hereinbelow, the risk that the fluid-carrying tubes will migrate or deviate from the prescribed pattern is reduced, thereby reducing the risk of misapplied thermal therapy.

Figure 5:
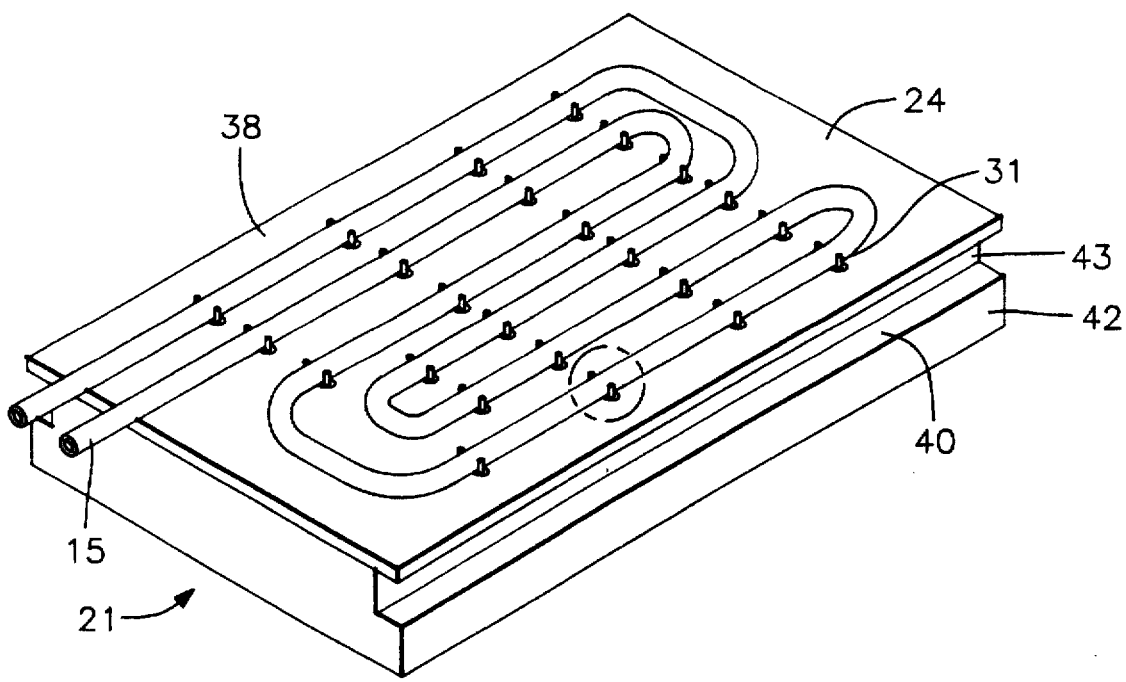
FIG. 5 is a simplified drawing of a typical tubing fixture and FIG. 5A is an enlarged drawing of an area encircled in FIG. 5.
Figure 5A:
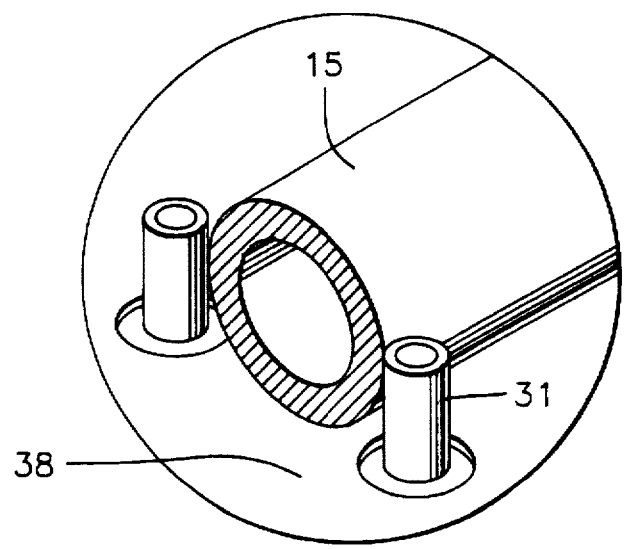

The following is a description of how the laminated pads, blankets or garments are manufactured. Multiple tubing fixtures are prepared for delivery to the main production line. FIG. 5 shows a typical tubing fixture 21, which comprises a base plate 40, having an array of tubing restraining pins 31, arranged in a pattern which is specific to the area of the human anatomy to be covered. The base plate 40 is shown to include a bottom plate portion 42 and a smaller recessed upper portion 43. This recess permits easier application and removal of the tubing release plate 38. The restraining pins 31 are fixed to the upper portion 43 of the base plate 40. A tubing release plate 38 is applied to overlie the base plate 40. The tubing release plate 38 includes a plurality of holes that coincide with the positioning of the restraining pins 31 and are of slightly larger diameter than the pin diameter as shown in the exploded view of FIG. 5A. The tubing release plate 38 is easily inserted over, and removable from, the base plate 40 and, when removed, serves to pull the tubing off of the base plate during the manufacturing phase after the tubing is transferred to the substrate fabric, in a manner to be described.

In the preferred embodiment of the invention, the tubing 15 is clear, plasticized, medical grade polyvinyl chloride (PVC), with a durometer (hardness) in the range of 55 to 70 Shore A and in the following size ranges, depending on the product: 0.050 to 0.150 inch inside diameter, and 0.100 to 0.200 inch outside diameter. The tubing restraining pins 31 are typically 0.063 inch diameter and are of such a length that the tubing 15 sits proud of the pins, i.e. extends above the pin ends, by about 25% of the tubing diameter in the tubing fixture 21, as shown in the exploded view of FIG. 5. Thus the pins 31 will not contact the substrate fabric when the tubing is transferred to the substrate fabric.

The tubing fixtures 21 serve the purposes of, a) restraining the tubing 15 in a predetermined serpentine configuration while the tubing is being thermally conditioned to stress relieve it and, b) provide a mechanism whereby the stress-relieved tubing can be transferred to the substrate fabric following adhesive application to the substrate fabric. It should be noted that the tubing fixtures are specific to the type of laminated pad, blanket, or garment being manufactured ie., there is a complete set of tubing fixtures for a knee pad which are different in size and tubing restraint layout from the fixtures required for, say, a wrist pad.

It will be appreciated that other tubing fixture constructions may be utilized. For example, in another embodiment (not shown), the tubing is held in a tubing fixture having semi-circular shaped grooves sized slightly larger than the tubing outside diameter to permit easy loading and unloading; the grooves having a series of small diameter holes at their base which penetrate to a vacuum chamber thereby providing an additional force to hold the tubing in place, the pattern of the grooves matching that of the desired tubing pattern. In yet another embodiment, the tubing is held in the tubing fixture using semi-circular shaped grooves sized slightly larger than the tubing outside diameter to permit easy loading and unloading and the tubing fixture is made of an electrically conductive material which can be electrically charged so as to impart an electrostatic force upon the tubing to maintain it in the grooves. Other arrangements that satisfy the purpose of restraining the tubing during the thermal treating process and the tubing removal process may be contemplated and within the scope of the present invention.

Figure 6:
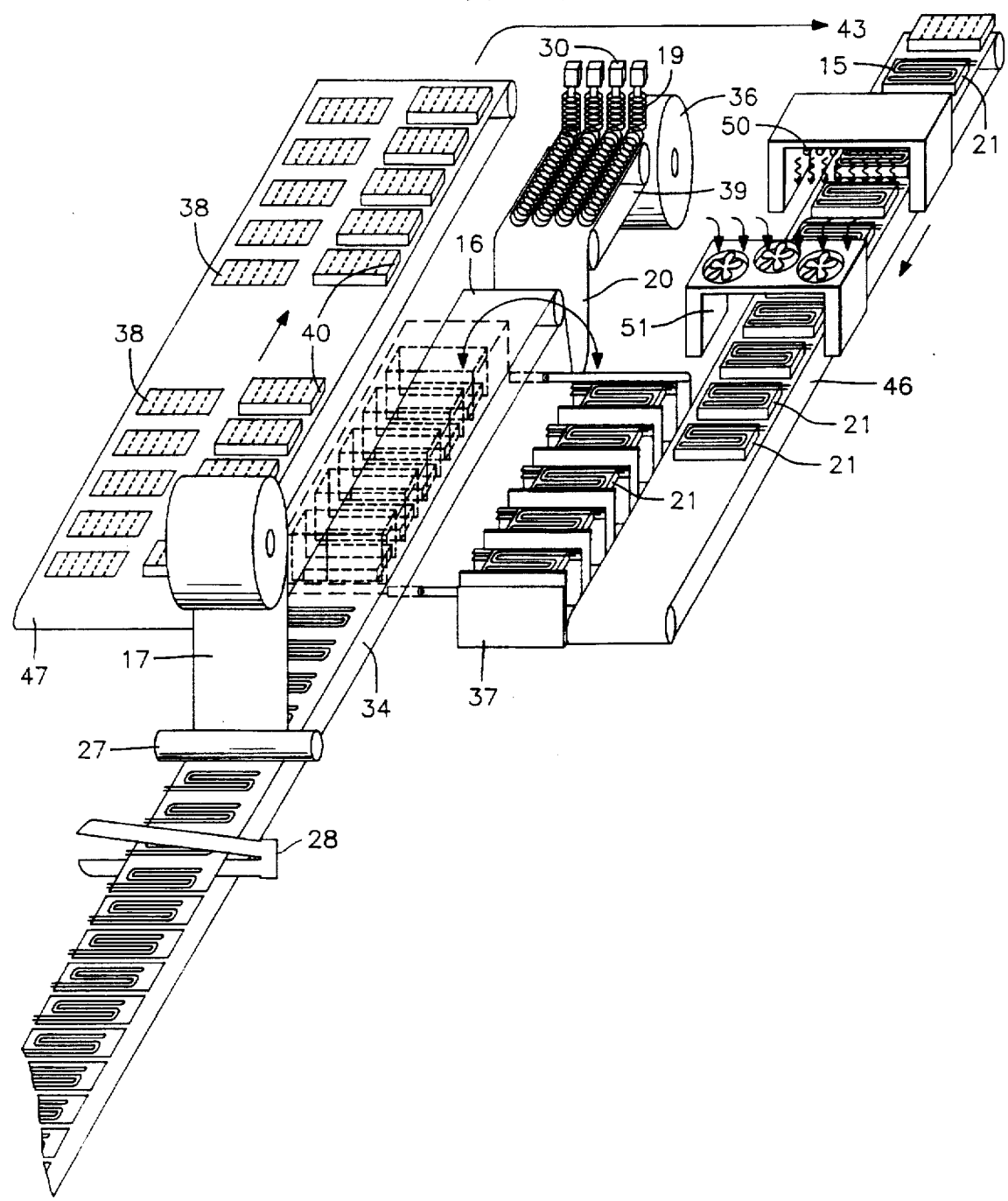
FIG. 6 is a representation of the manufacturing process.

The complete tubed lamination heat transfer pad manufacturing process, in the preferred embodiment, is shown in FIG. 6. The tubing fixtures are prepared in a three step process. First, the tubing fixtures 21 are manually or robotically loaded with tubing 15, in the predetermined pattern. That is, predetermined lengths of tubing are inserted between the tubing restraining pins 31 by threading or pressing the tubing between the pins to form loaded tubing fixtures of the type depicted in FIG. 5. Next the tubing is brought up in temperature to approach or reach the normal processing temperature, or temperature at which the plastic tubing material becomes soft and moldable, but not so high as to melt the material or distort the overall profile of the tubing. In the case of plasticized PVC tubing this temperature is about 300° F. and is reached by passing the loaded tubing fixtures under a radiant heater 50, with the tubing directly facing the heater. Finally the tubing is cooled as the tubing fixtures pass through a forced-air cooling chamber 51. Once cooled, the tubing retains its new shape and is substantially stress-relieved, no longer exhibiting a tendency to straighten out, although, it does remain in the tubing fixture until it is transferred to the adhesive-coated substrate fabric on the main production line. Prepared tubing fixtures are delivered to the main production line via a conveyor belt 46, although other delivery methods, including manual delivery to the main production line, may be employed.

The substrate fabric 16, which is in the form of a roll 36, which has been pre-cut to the appropriate width, is delivered to a constant feed conveyor 39, and passed underneath the adhesive applicator 30. Polyurethane adhesive (PUR) is heated to approximately 225° to 250° F. in the applicator and uniformly deposited upon the substrate at a rate of about 2 to 4 grams per square foot in a prescribed circular pattern 19, which minimizes effects on the porosity of the substrate fabric. That is, the adhesive is applied in an amount and pattern that does not significantly interfere with the vapor and air permeability of the fabric substrate. The preferred PUR is a BONDMASTER ADHESIVE from National Starch and Chemical Company which goes by the registered tradename PUR-FECT LOK 70-7799 and the preferred application system is the NORDSON CF-2000 Series Controlled Fiberization System. The PUR comes out of the applicator as a very fine monofilament strand, typically 0.012 inches diameter, and actually cools before reaching the substrate yet remains tacky for about 0.5 to 1.5 minutes (termed the "open" time), which is adequate to execute the balance of the lamination process. The open time of the PUR is controlled for reasons and in a manner to be described. The fact that the PUR is applied at substantially room temperature allows for the use of virtually any substrate or liner fabric, even very thin, heat sensitive materials. Very thin fabrics are desirable for many products for the many reasons mentioned above, such as performance and cost. The substrate fabric, as well as the liner fabric are to be substantially permeable to vapor and air and flexible to conform to the body and body movement.

Figure 7A:
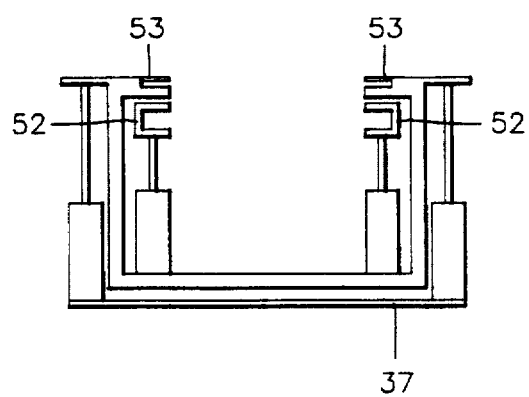
FIG. 7 (including FIGS. 7A–7F) is an end view of the fixture holder during the actuation process.
Figure 7D:
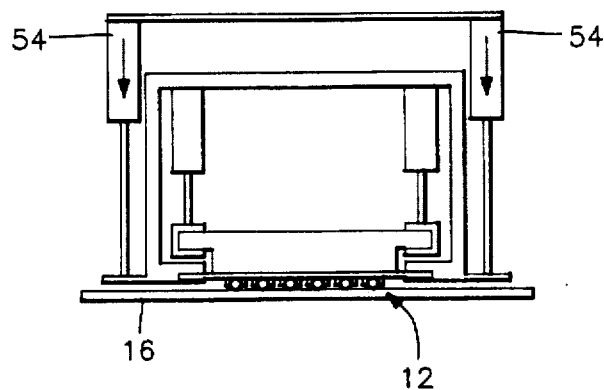
Figure 7B:
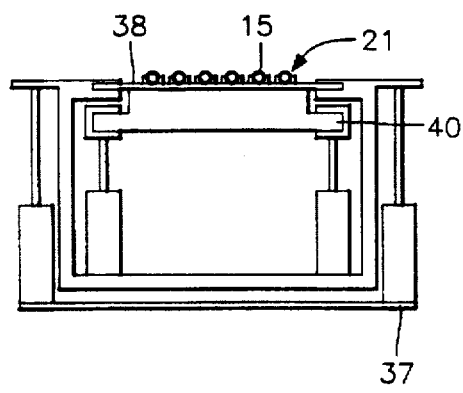
Figure 7E:
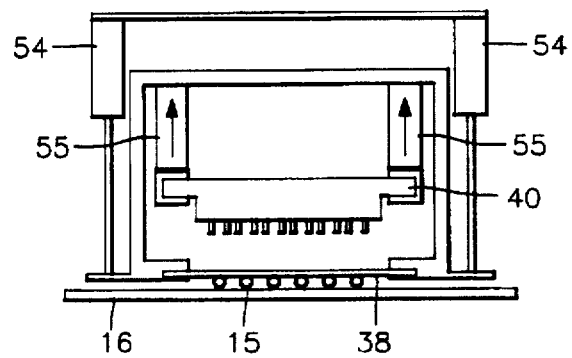
Figure 7C:
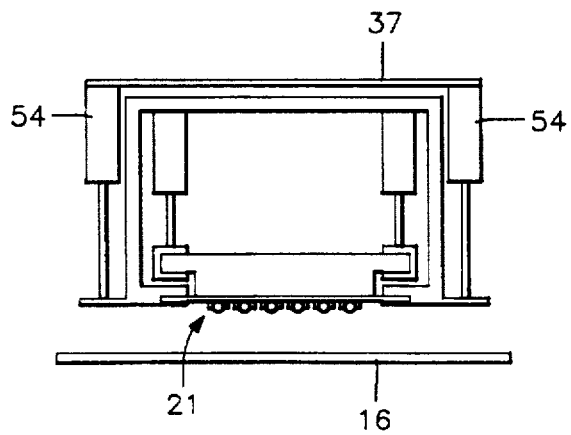
Figure 7F:
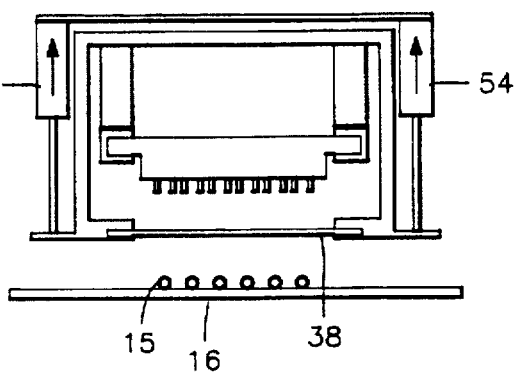

Following adhesive application the substrate fabric is allowed to form an index compensation loop 20, as the production line, or substrate fabric, changes to an indexed conveyor system shown schematically at 34. An indexed conveyor system is well known and provides for periodic movement at predetermined, adjustable rates. It is during the period of time when there is no movement of fabric on the indexed conveyor, that a plurality of the prepared tubing fixtures 21 are loaded onto a fixture holder 37. This loading can be done manually or automatically by known mechanical means. Once all tubing fixtures 21 are in place, the fixture holder 37 is actuated such that it rotates and inverts the fixtures to be oriented in a tubing-to-substrate position, and in part of the same motion, presses all the fixtures down, with a preset, controlled force upon the tacky adhesive-coated substrate fabric. It is important to note that no heat is applied at this point to make the tubing stick to the substrate; the adhesion takes place at substantially room temperature. FIG. 7 shows a detail of how the tubing fixtures are held in the fixture holder and the steps in the actuation process. FIG. 7A shows an end view of a single section of the fixture holder 37 positioned ready to be loaded. The tubing fixture 21 (made up of the base plate 40 and tubing release plate 38) slides into holding rails 52 and 53. FIG. 7B shows the tubing fixture 21 loaded with tubing 15 installed in the fixture holder 37 ready for actuation. FIG. 7C shows the fixture holder 37 now inverted and positioned above the substrate fabric 16 immediately prior to being pressed down onto the substrate fabric. FIG. 7D shows the tubing fixture 21 being pressed down onto the substrate fabric 16 by the fixture actuators 54, which are air or hydraulic cylinders or other such linear actuating mechanisms. FIG. 7E shows the tubing release plate 38 and tubing 15 still being held down by the fixture actuators 54 while the base plate 40 is retracted by the base plate actuators 54, which are also air or hydraulic cylinders or other such linear actuators. FIG. 7F shows the retraction of the tubing release plate 38 by the fixture actuators 54 such that the tubing 15 is left behind, stuck to the adhesive coated substrate fabric 16. The base plates and the tubing release plates can then be individually removed manually, or by known mechanical means, and placed on another conveyor 47, shown in FIG. 6, which returns them to the tubing loading station 43. The substrate fabric is then advanced by the indexed amount, which is dependent upon the number of fixtures being used.

The preferred PUR adhesive must be tacky or still in its open time at this point to keep the tubing in position and to complete the lamination process. It is therefore desirable to have control over the PUR open time. This is achieved by altering the humidity and/or the temperature, locally. We have found for example that it is relatively easy to maintain dry conditions to extend the open time of the adhesive (it is cured by moisture) and simply add moisture through misting once the lamination process has been completed. Similar effects can be achieved by raising or lowering the local air temperature or the substrate fabric temperature.

Following the application of the tubing to the substrate fabric, the liner fabric 17, is introduced and made to come in contact with the substrate fabric, in an aligned fashion. The three components of the lamination, the substrate fabric 16, the stress-relieved tubing 15, and the liner fabric 17, are pressed together using one or more soft compression rollers 27, only of which one is depicted. The soft compression rollers are covered in a foam material and their purpose is to provide the pressure required to bring the adhesive coated substrate fabric in intimate contact with liner fabric thereby providing a bond to each without damage to the tubing. This pressure application also provides a positive bond of the tubing to the substrate fabric. The substrate and liner are adhesively bonded to each other to envelop and surround the tubing and retain the tubing in position. The tubing may also be adhesively bonded to the substrate and/or liner. The application of pressure between the substrate and liner is unaccompanied by the application of heat. The laminated strip is then sheared to finished sized pieces by a powered knife 28, and are delivered for secondary processing such as trimming, tubing connector attachment, testing and packaging.

It should be emphasized that the adhesive bonding of the substrate and fabric with the polyurethane adhesive is unaccompanied by any heat fusion. That is, neither the substrate nor liner requires heat fusible fabrics, the adhesive is not required to be a heat fusible adhesive, and, thus, there is no heat fusion bonding of the fabrics to each other or to the tubing.

Having above indicated a preferred embodiment of the present invention, it will occur to those skilled in the art that modifications and alternatives can be practiced within the spirit of the invention. It is accordingly intended to define the scope of the invention only as indicated in the following claims.

What is claimed is:

1. A heat transfer pad, blanket, or garment comprising,
   stress-relieved flexible tubing disposed in a self-sustaining serpentine configuration without being externally supported and adapted to receive heating/cooling fluids therethrough;
   a first flexible fabric substantially permeable to vapor and air; and
   means for supporting said stress-relieved flexible tubing to said first flexible fabric.

2. The pad, blanket, or garment of claim 1 wherein said means for supporting comprises an adhesive material to adhesively bond said tubing to said first flexible fabric.

3. The pad, blanket, or garment of claim 1 wherein said means for supporting comprises a second flexible fabric substantially permeable to vapor and air, said tubing sandwiched between said first and second flexible fabrics, said first and second flexible fabrics adhesively bonded to each other.

4. The pad, blanket, or garment of claim 3 wherein said stress-relieved flexible tubing is formed by shaping and restraining an elongated flexible plastics tubing into a serpentine configuration, heating the serpentine-shaped tubing to a temperature whereby the tubing substantially retains its serpentine configuration in an unrestrained condition, and then cooling the tubing, whereby the cooled serpentine-shaped tubing is in a substantially stress-relieved condition.

5. The pad, blanket, or garment of claim 3 wherein said first and second flexible fabrics are bonded by a polyurethane adhesive.

6. The pad, blanket, or garment of claim 5 wherein said first and second flexible fabrics envelop and surround said tubing to retain said tubing in position between said first and second flexible fabrics.

7. The pad, blanket, or garment of claim 3 wherein said tubing is adhesively bonded to at least one of said first and second flexible fabrics.

8. The pad, blanket, or garment of claim 3 wherein said first and second flexible fabrics are adhesively bonded to each other by applying, in a substantially uniform pattern, adhesive material to said first fabric, positioning said stress-relieved flexible tubing on said adhesive-applied first flexible fabric, overlaying said second flexible fabric on said flexible tubing, and applying pressure between the first and second flexible fabrics.

9. The pad, blanket, or garment of claim 3 further comprising a temperature sensor disposed between the first and second flexible fabrics, and not in contact with said tubing, said sensor having electrically conductive leads extending out of the fabric.

10. The pad, blanket, or garment of claim 3 wherein said first and second flexible fabrics are not heat fused to each other or to the tubing.

11. The pad, blanket, or garment of claim 3 wherein said serpentine tubing configuration conforms to a part of the human anatomy.

12. The pad, blanket, or garment of claim 3 wherein said flexible tubing is a plasticized polyvinyl chloride plastics material.

13. A laminated fabric product having a flexible fabric substrate, a flexible fabric liner and a stress-relieved flexible tubing disposed in a self-sustaining serpentine configuration sandwiched between said substrate and liner, said flexible fabric product for use in forming heating/cooling pads, blankets, or garments, said laminated fabric product formed by the process of:

(a) forming a stress-relieved, self-sustaining flexible tubing disposed in a serpentine configuration upon a tubing fixture by the steps of;
      (1) providing a tubing fixture having tubing retaining means for receiving and retaining flexible plastic tubing in a predetermined serpentine configuration,
      (2) inserting the tubing into said tubing retaining means to orient said tubing in the predetermined serpentine configuration and to restrain the tubing into said predetermined serpentine configuration,
      (3) heating the restrained tubing to a temperature sufficient to impart a memory to said tubing so that the tubing is in a substantially stress-relieved condition, and,
      (4) cooling the tubing;
   (b) providing a flexible fabric substrate that is substantially permeable to vapor and air;
   (c) applying adhesive material, in a substantially uniform pattern, to the flexible fabric substrate in an amount and pattern that does not significantly interfere with the vapor and air permeability of the fabric substrate;
   (d) orienting the tubing fixture to overlie the fabric substrate such that the flexible tubing faces the applied adhesive material surface of the fabric substrate;
   (e) moving the tubing fixture in the direction toward the fabric substrate such that the flexible tubing contacts the adhesive material surface of the fabric substrate;
   (f) releasing the flexible tubing from the tubing fixture so that the serpentine-shaped tubing is supported upon the fabric substrate;
   (g) providing a flexible fabric liner overlying the tubing and fabric substrate;
   (h) applying pressure between the fabric liner and fabric substrate to adhesively bond the fabric liner to the fabric substrate so that the stress-relieved, self-sustaining tubing is retained therebetween, to thus form the laminated fabric product.

14. The laminated fabric product formed by the process of claim 13 wherein said step of applying adhesive material comprises applying a polyurethane adhesive at substantially room temperature.

15. The laminated fabric product formed by the process of claim 14 wherein the applying of pressure between the fabric liner and fabric substrate is unaccompanied by the application of heat.

16. The laminated fabric product of claim 15 wherein the applying of pressure between the fabric liner and fabric substrate is unaccompanied by any heat fusing of the fabrics to each other or to the tubing.

* * * * *